United States Patent [19]

Radowsky, Jr.

[11] Patent Number: 4,479,267

[45] Date of Patent: Oct. 30, 1984

[54] SAFETY HARNESS

[76] Inventor: Peter Radowsky, Jr., 1879 Saunders Settlement Rd., Niagara Falls, N.Y. 14304

[21] Appl. No.: 473,069

[22] Filed: Mar. 7, 1983

[51] Int. Cl.³ ........................ A41D 13/00; A61F 5/02; A61D 19/00

[52] U.S. Cl. ................................................ 2/2; 2/44; 2/337

[58] Field of Search ..................... 2/2, 46, 44, 45, 337, 2/338, 321, 311; 128/78

[56] References Cited

U.S. PATENT DOCUMENTS

| | | | |
|---|---|---|---|
| 3,089,143 | 5/1963 | Jacobson | 2/1 |
| 3,554,190 | 1/1971 | Kaplan | 2/44 |

*Primary Examiner*—Doris L. Troutman

[57] ABSTRACT

The present harness comprises a pair of shoulder straps secured to a belt. The shoulder straps are crossed in the back similar to a pair of suspenders. However, unlike a pair of suspenders, the shoulder straps are not secured at the point of crossing. The belt portion is adapted to be secured around the wearer's waist.

The belt and shoulder straps are fabricated of a flexible material, suitably of plastic, or combinations thereof, or canvas, particularly suited is belting such as web belting. The belt and shoulder straps have a reflective surface on the outer portion thereof to reflect light striking such surface.

5 Claims, 1 Drawing Figure

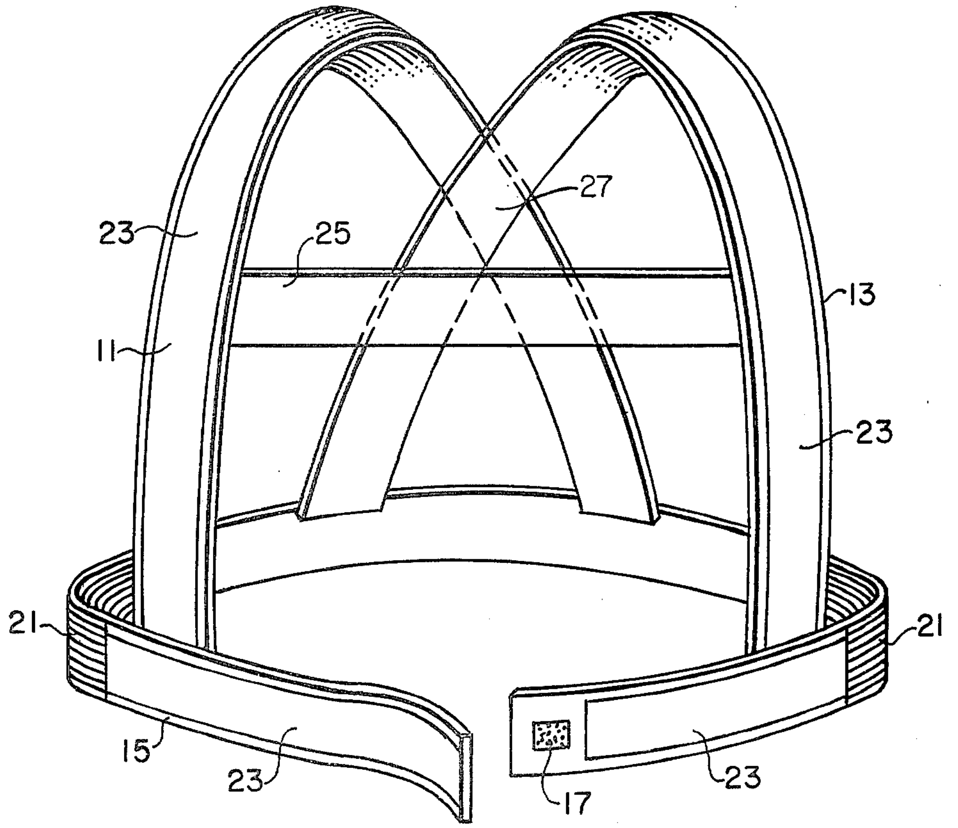
23
25
27
13
11
23
21
21
15
23
17
23

SAFETY HARNESS

BACKGROUND OF THE INVENTION

The present invention relates to the general field of safety clothing, and more particularly to a reflective harness adapted to be worn over an outer garment by persons exposed to night-time dangers, for example confrontation with a moving vehicle.

Almost every automobile operator while driving in darkness or semi-darkness has experienced the sudden realization that a pedestrian or bicyclist is sharing the immediate roadway. Such realizations cause sudden swerves or stops with results ranging from minor irritation to injury or death. The present invention provides a reflective harness designed to alleviate such situations.

There are safety vests presently available on the commercial market. These vests are fabricated of plastic or a fluorescent or reflective nature and may be seen in use by flagman, highway workers and fireman.

The prior art ranges from vests which are illuminated, of which U.S. Pat. No. 4,328,511 issued May 4, 1982 to Paredes is an example, to reflective safety bands, of which U.S. Pat. No. 3,499,416 issued Mar. 10, 1970 to Thorsheim is an example. However, none of the available or prior art articles are adapted to be utilized by persons engaging in activities requiring a large degree of freedom of movement, for example, hikers, joggers, bikers, motorcyclists, traffic coordinators, railroad or airline workers.

The present safety harness is designed to allow the wearer a maximum freedom of movement and may be used with the wearer's normal outer clothing giving the wearer his choice of clothing suitable for use in various weathers.

The present reflective safety harness may also be used as a means of identification under semidarkness and darkness conditions. For example, police and fireman may wear harnesses having different reflective properties at accident, fire or emergency scenes allowing instant and distant identification of the service of the individual wearing the harness. The present reflective harness is equally useful in the military service allowing the location of the individual and identification of his or her function or capacity to be determined instantly.

The present harness may also be adapted to animals, such as K-9 or police dogs or seeing-eye dogs, and may also be utilized on pet animals to provide night-time protection.

The present reflective harness gives high visibility in darkness or semi-darkness. It is light in weight and comfortable to wear. It may be easily put on or taken off. It is easily stored. It provides an efficient and inexpensive measure of protection of the individual from night-time hazards.

BRIEF DESCRIPTION OF THE INVENTION

The present harness comprises a pair of shoulder straps secured to a belt. The shoulder straps are crossed in the back similar to a pair of suspenders. However, unlike a pair of suspenders, the shoulder straps are not secured at the point of crossing. The belt portion is adapted to be secured around the wearer's waist by means of a fastening device, for example a snap or buckle but more preferably by meshing friction surfaces, for example, a woven nylon hook and loop fastener such as that presently marketed under the trademark of Velcro. The belt preferably has sections of elastic positioned in the sides of the belt to enable the wearer to freely move without dislocating the belt from the wearer's waist.

The belt and shoulder straps are fabricated of a flexible material, suitably of plastic, or combinations thereof, or canvas, particularly suited is belting such as web belting. The belt and shoulder straps have a reflective surface thereon adapted to reflect light striking such surface.

The reflective surface may also be fluroscent to provide added visibility under partial daylight conditions such as dawn or dusk. The reflective surface preferably remains highly reflective surface preferably remains highly reflective when viewed at wide entrance angles between about −4 and 40 degrees. The angle formed by a light beam striking a surface at some point and a line perendicular to the surface at the same point. Suitable films and fabrics are presently produced by 3M Corporation under the trademark Scotchlite.

The present harness may have two reflective surfaces thereon and be made reversible. Thus, for example, one side may reflect yellow and the other white which would allow members of an operating group or team, for example, servicemen, fireman, or policemen, to identify and locate the various functional members and for the members to give notice of their assumption or change of duties by simple reversal of their harness.

In an alternative mode of the present harness, a chest strap may be utilized to connect the front portions of the shoulder strap. The chest strap is detachably secured suitably by meshing friction surfaces across the shoulder straps and provides additional stability and may provide an additional reflective surface.

DETAILED DESCRIPTION OF THE INVENTION

The present invention will now be described in detail by reference to the accompanying drawing which is a frontal view in prospective of the harness.

Looking now at the drawing, shoulder straps 11 and 13 are secured to belt 15 and the combination is adapted to be worn by a person by merely placing their arms in the shoulder straps and fastening the belt around the wearer's waist, much in the manner in which a person would put on a vest. Shoulder straps 11 and 13 pass in a free manner, that is they are not secured at their crossing point 27. Belt 15 has a fastening means 17 thereon, preferably in the front allowing the wearer to secure himself in the harness. Belt 15 preferably has elastic portions 21 therein to better secure the belt around the wearer's waist during movement. The belt and shoulder strap width may vary. Widths ranging from ¾ inch to 2 inches are useful, widths between 1 and 1½ inches are better adapted and a width of about 1¼ inches has been found to be particularly useful.

The outside surfaces of belt 13 and shoulder straps 11 have a reflective surface 23 thereon. Preferably the reflective surface is in the form of a strip of a film fabric attached, suitably by sewing, onto the belt and shoulder straps. Although the reflective surface may cover the entire outer surface of the belt and shoulder straps, it is preferred that the reflective surface extend only to a distance from about ⅛ to about ¼ inch from the edges of the belt and shoulder straps, generally varying between about ½ to about 1½ inches in width. Shoulder straps 11 and 13 are spacedly positioned along belt 15 to provide a cage arrangement. That is, as measured from an end of the belt, on shoulder strap is attached to the belt at a point about $\frac{1}{8}$ along the belts length and at another point about $\frac{5}{8}$ along the belts length. The second shoulder strap is attached at a point about $\frac{3}{8}$ along the belts length and at a second point about $\frac{7}{8}$ along the belts length.

The drawing also shows an alternative mode of the invention wherein an optional chest strap 25 which is detachedly secured to shoulder straps 11 and 13 across the front of the harness at chest level of the wearer. The chest strap allows additional stability of the harness when the wearer is engaged in activities such as motorcycle riding, as either operator or passenger, or in requiring lesser movement such as stationary guards. The chest strap may also provide additional reflective surface.

The foregoing description and embodiments are intended to illustrate the invention without limiting it thereby. It will be understood that various modifications can be made without departing from the spirit or scope thereof.

What is claimed is:

1. A safety harness having a front and a back portion comprised of (a) a belt (b) a belt fastening means adapted to secure said belt around a wearer's waist, said belt having elastic portions positioned in the sides thereof, (c) a pair of shoulder straps spacedly secured to said belt at said front and back portions of said harness, said shoulder straps singly crossing in the back of said harness in a free manner, (d) a reflective surface on the outer portions of said belt and said shoulder straps.

2. The harness of claim 1 wherein said belt fastening means is in the form of engagable mesh surfaces.

3. The harness of claim 1 wherein a chest strap is detachably secured to said shoulder straps at the front portion of said harness.

4. The Safety harness of claim 1 wherein the reflective surface has a width between about $\frac{1}{2}$ and $1\frac{1}{2}$ inches.

5. The safety harness of claim 1 wherein the inside and outside of said belt and said shoulder straps has a reflective surface thereon.

* * * * *